United States Patent
Boltz

(10) Patent No.: US 6,752,002 B2
(45) Date of Patent: Jun. 22, 2004

(54) SENSOR

(75) Inventor: Eric S. Boltz, Cincinnati, OH (US)

(73) Assignee: Marathon Sensors, Inc., Cincinnati, OH (US)

( * ) Notice: Subject to any disclaimer, the term of this patent is extended or adjusted under 35 U.S.C. 154(b) by 18 days.

(21) Appl. No.: 10/289,196

(22) Filed: Nov. 6, 2002

(65) Prior Publication Data

US 2003/0084706 A1 May 8, 2003

Related U.S. Application Data

(60) Provisional application No. 60/355,255, filed on Jun. 11, 2001.

(51) Int. Cl.[7] .............................................. G01N 27/416
(52) U.S. Cl. ...................... 73/23.2; 73/23.31; 73/31.05; 204/409; 204/428
(58) Field of Search .............................. 73/23.2, 23.32, 73/31.05, 23.31; 204/428, 409

(56) References Cited

U.S. PATENT DOCUMENTS

| | | | |
|---|---|---|---|
| 3,773,641 A | 11/1973 | Fitterer | 204/423 |
| 4,101,404 A * | 7/1978 | Blumenthal et al. | 204/428 |
| 4,193,857 A * | 3/1980 | Bannister et al. | 204/428 |
| 4,198,279 A | 4/1980 | Brown et al. | 204/408 |
| 4,284,487 A | 8/1981 | Barnes et al. | 204/408 |
| 4,290,586 A | 9/1981 | Kane et al. | 266/80 |
| 4,320,378 A * | 3/1982 | Taniguchi et al. | 338/34 |
| 4,485,002 A * | 11/1984 | Wunning | 204/428 |
| 4,507,192 A * | 3/1985 | Ebizawa et al. | 204/428 |
| 4,588,493 A * | 5/1986 | Blumenthal et al. | 204/428 |
| 4,814,061 A | 3/1989 | Blumenthal et al. | 204/410 |
| 4,916,934 A * | 4/1990 | Nagata et al. | 204/428 |
| 5,012,670 A * | 5/1991 | Kato et al. | 73/31.05 |
| 5,324,415 A | 6/1994 | Blumenthal et al. | 204/427 |
| 5,635,044 A * | 6/1997 | Lotze et al. | 204/428 |
| 5,851,369 A | 12/1998 | Cai | 204/428 |

* cited by examiner

Primary Examiner—Daniel S. Larkin
(74) Attorney, Agent, or Firm—Dinsmore & Shohl LLP

(57) ABSTRACT

A sensor having a conductive protective sheath, an internal sensor element, and a conductive end cap. The conductive end cap is connected to the distal end of the conductive protective sheath and is in contact with the internal sensor element. The conductive protective sheath has a plurality of apertures symmetrically arranged to prevent fluid flow in a straight direction of a sample fluid through the conductive protective sheath. A sensor having a conductive protective sheath, an internal sensor element, and a conductive end cap. The conductive end cap is connected to the distal end of the conductive protective sheath. The conductive end cap one or more contact areas from the group including a side contact area, an upper contact area, and an internal indentation contact area. The internal sensor is in contact with at least one of the contact areas of the conductive end cap.

14 Claims, 2 Drawing Sheets

SENSOR

This application claims the benefit of provisional application No. 60/333,255 filed Jun. 11, 2001.

TECHNICAL FIELD

The present invention relates to sensors for determining the concentration of a constituent of a fluid stream, such as an oxygen sensor for monitoring of atmosphere in industrial processes. In the present invention, apertures, formed in a three-fold symmetrical arrangement, may be located in a conductive protective sheath to impede laminar flow near the tip of the sensor element, thus improving the accuracy of the sensor. In addition, the sensor tip may, without modification, allow the sensor to accommodate more than one type of sensor element.

BACKGROUND OF THE INVENTION

Solid-state electrolyte sensors are commonly used for monitoring and control of a number of different industrial atmospheres; one example is an oxygen sensor. Although termed "oxygen sensors", these devices are actually sensitive to a number of variables. In highly reducing atmospheres (very low oxygen with chemical species present that readily react or "reduce" oxygen), these types of sensors do not, in fact, measure oxygen levels. Instead, under such conditions, they are a measure of the reduction potential of the gas. In other words, they measure the rate at which the atmosphere can reduce oxygen ions that transit the zirconium oxide cell.

To further complicate the situation, these sensors are also highly sensitive to kinetic elements of the atmosphere. When a gas moves quickly it can more efficiently remove and reduce oxygen ions even though its composition does not change. In many furnaces where such probes are used, the high volume of gas flow in the furnace creates laminar flow over the tip of the sensor. This flow can result in false low readings of oxygen or reduction potential (or carbon potential as it is commonly referred to in the heat-treating market). Conventional sensor designs expose the tip of the substrate via a number of holes or slots cut in a protection tube most commonly fabricated of stainless steel (RA330 is most common). This type of "ventilation" is considered very important in avoiding a build up of oxygen inside the protective sheath. Unfortunately, the geometry employed for this "ventilation" allows laminar flows to travel into and through the probe, negatively affecting accuracy.

Additionally no sensor tip design, to date, has been able to accommodate more than one type of sensor element. As there are three standard types of zirconia substrates commonly used in oxygen sensors, as well as new element designs currently under development, a need exists for a single sensor tip design which will readily accept more than one type of sensor element.

Thus, there is a need for a sensor design that may impede laminar flow travel into and through the probe, and for a sensor tip that may accommodate more than one type of sensor element, particularly one which may accept any of the three standard types of zirconia substrates commonly used in oxygen sensors.

SUMMARY OF THE INVENTION

Accordingly, it is an object of the present invention to obviate problems of the prior art. It is a related object of the present invention to provide a sensor that impedes laminar flow and promotes turbulent flow over the tip of the sensor element. It is an additional object of the present invention to provide a sensor that may accommodate a broad range of zirconium oxide sensor elements (also referred to as "substrates") without requiring modification or additional parts.

The design of the present invention includes a unique, three-fold symmetry for ventilation that impedes laminar flow and promotes turbulent flow over the tip of the sensor element. As a result, this design is significantly more accurate in environments where laminar flow of gases is found. If flow patterns result in abnormally high kinetic contribution to the sensor signal on one side of the probe, the lack of through-flow in a sensor of the present invention results in a comparable reduction of kinetic contribution on the opposite side of the probe.

A further innovation of the new tip design is a internal geometry that readily accepts any of the three standard types of zirconia substrates commonly used in oxygen sensors as well as new element designs currently under development. To date, no sensor tip design has been able to accommodate more than one type of sensor element.

BRIEF DESCRIPTION OF THE DRAWINGS

While the specification concludes with the claims particularly pointing out and distinctly claiming the present invention, it is believed that the same will be better understood from the following description taken in conjunction with the accompanying drawings in which:

DETAILED DESCRIPTION

The design of the present invention may include three-fold symmetrical ventilation that impedes laminar flow and promotes turbulent flow around the tip of the internal sensor element. As a result, this design is significantly more accurate in environments where laminar flow of gases is found. If flow patterns result in abnormally high kinetic contribution to the sensor signal on one side of the probe, the lack of through-flow provided by the present invention results in a comparable reduction of kinetic contribution on the opposite side of the probe.

As is known to those skilled in the art, electrolytic sensors (such as oxygen sensors) typically include an internal sensor element (or "substrate") comprising an electrolyte material (such as zirconia). An internal electrode is located within the interior of the internal sensor element, and reference air is also supplied to the interior of the internal sensor element. The internal sensor element is typically positioned within a conductive outer sheath which not only protects the internal sensor elements but also acts as the second electrode. Apertures in the sheath allow the fluid to be tested to enter the space between the sheath and the internal sensor element.

Figure 1:
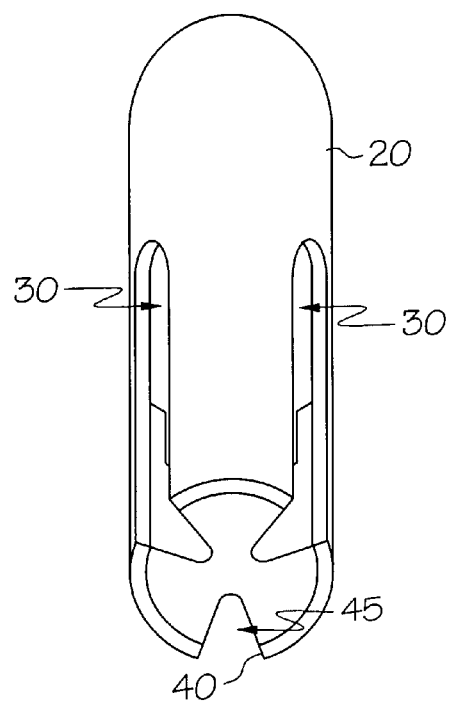
FIG. 1 is a perspective end view of the distal end of a conductive sheath for a sensor according to the present invention.
Figure 2:
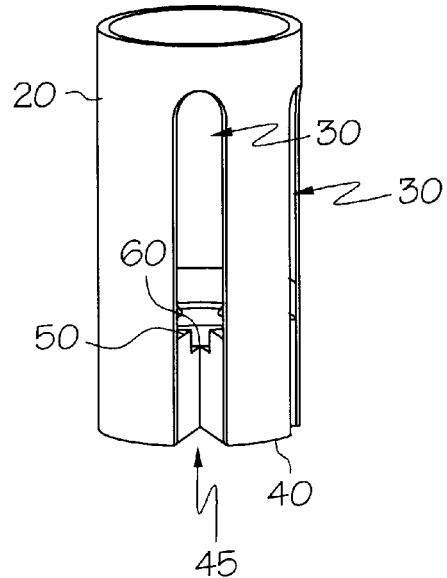
FIG. 2 is a perspective view of the distal end of the conductive sheath of FIG. 1.

The present invention provides an unique outer sheath and tip which improves fluid flow and/or allows for the use of a variety of internal sensor elements. It should be pointed out that only the distal end portion of the sensor is depicted herein, as the remainder may have any well-known configuration. Outer sheath 20 is depicted in FIG. 1, and is sized to accommodate an internal sensor element therein. The conductive protective sheath 20 not only protects the inner sensor element, but also acts as a second electrode. The conductive protective sheath 20 contains apertures 30 adjacent the distal end of the conductive protective sheath 20, near the sensor tip 40. Apertures 30 may be provided in a three-fold symmetrical arrangement, wherein apertures 30 are arranged symmetrically about the outer circumference of sheath 20. Because of this arrangement, fluid being tested cannot flow straight through sheath 20, thus promoting turbulent flow about the tip of the inner sensor element by preventing direct air flow through the end of the conductive protective sheath 20.

Figure 4:
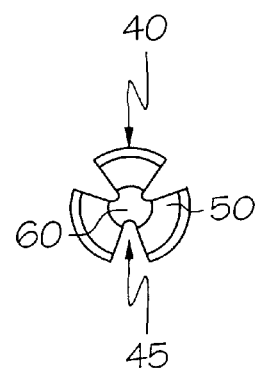
FIG. 4 is a schematic end view of the sensor tip of FIG. 3, taken along line 4—4 thereof.

The sensor tip (or conductive end cap) 40 may also reflect the three-fold symmetrical arrangement of the apertures 30, as shown in FIG. 4. In this drawing, three cut-outs 45 are indicated; the sensor tip 40 may have portions removed, the aforementioned cut-outs 45, to coincide with the apertures 30 in the conductive protective sheath 20, thus allowing greater air contact with and promoting turbulent flow about the tip of the sensor element. While the sensor tip 40 is located within conductive protective sheath 20 which may be cylindrical, the sensor tip 40 is not required to have such a cylindrical structure, so long as it securely fits within the conductive protective sheath 20.

Tip 40 not only serves to protect the inner sensor element (or substrate), it also provides electrical contact between the inner sensor element and the conductive sheath. Therefore, it is important to provide good electrical contact between the distal end of the inner sensor element and the tip.

Figure 3:
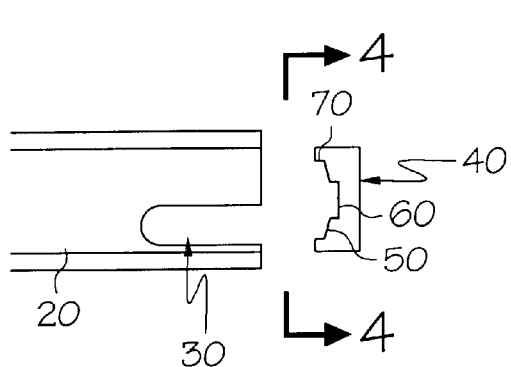
FIG. 3 is a partial cross-sectional schematic view of the conductive sheath of FIG. 1. In this drawing, the sensor tip is separated from the conductive sheath to better illustrate the structure of the sheath. In addition, only one aperture is shown for purposes of clarity.

The three major classes of sensor elements are SIRO, round slip-cast, and flat slip-cast. To date, no sensor tip design has been able to accommodate more than one type of sensor element. A further innovation of the present invention is a internal geometry for the tip that readily accepts any of the three standard types of zirconia substrates commonly used in oxygen sensors, as well as new element designs currently under development. FIG. 3 shows the sensor tip 40 of the present invention separated from the protective sheath 20. The sensor tip 40 may include three separate types of contact area: upper contact areas 50, side contact areas 70, and an internal indentation contact area 60. This configuration allows the tip of the sensor element to contact the upper contact area 50, the side contact area 70, the internal indentation contact area 60, or a combination of two or more of these areas.

Figure 5A:
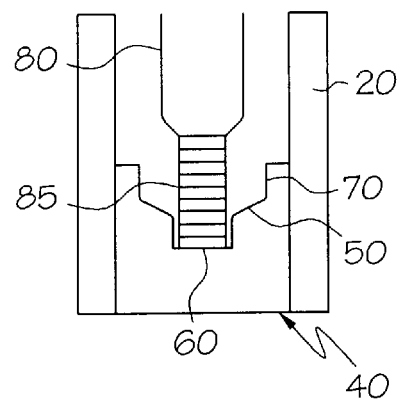
FIG. 5A is a partial cross-sectional schematic view of a sensor according to one embodiment of the present invention which employs a SIRO sensor element.

SIRO is a sensor design which originated at CSIRO, a government laboratory in Australia. The SIRO design uses a small piece of zirconium oxide that is cemented into one end of an aluminum oxide tube. This design has both reduced cost and increased thermal ruggedness when compared to other types of sensor elements. Sensor tip designs for SIRO-based products use one of two approaches. The first method for contacting the outer side of the SIRO is to wrap a wire around the zirconium end piece. The second, and by far more common method, is to machine a cylindrical recession into a conductive protection sheath. When the probe is assembled the SIRO end-piece sits in this recession and is, in all known cases, spring loaded to ensure good contact with the sheath. The sheath then acts as the outer electrode. In the sensor shown in FIG. 5A, a SIRO sensor element 80 is placed within the conductive protective sheath 20. The tip 85 of the SIRO sensor element 80 fits within the internal indentation 60 of the sensor tip 40, allowing contact between the tip 85 of the sensor element 80 and the walls of indentation 60 of sensor tip 40. Since tip 40 is positioned within the distal end of sheath 20 in electrical contact therewith (e.g., by cementing tip 40 in place), the conductive protective sheath 20 acts as a second electrode for the sensor.

Figure 5B:
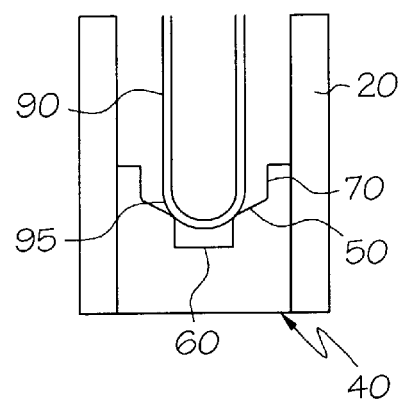
FIG. 5B is a partial cross-sectional schematic view of a sensor according to one embodiment of the present invention which employs a round slip-cast sensor element.

A slip-cast substrate is one that is made entirely of zirconium oxide using a process commonly referred to as slip casting. This technology provides a faster response than the SIRO design but is much more susceptible to thermal and mechanical shock. The "round slip-cast" design refers to sensor elements that have a round geometry at the closed (or distal) end of the sensor tube. Of the two categories of slip-cast elements, rounded end designs are less expensive owing to higher yield in producing this design. In the sensor shown in FIG. 5B, a round slip-cast sensor element 90 is placed within the conductive protective sheath 20. The distal end 95 of the round slip-cast sensor element 90 contacts the sensor tip 40 at the edges of upper contact area 50 adjacent indentation 60, thus permitting the conductive protective sheath 20 to act as a second electrode.

Figure 5C:
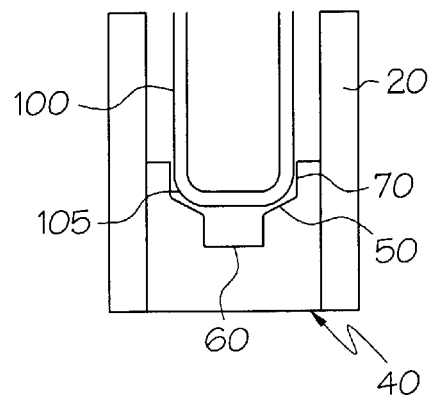
FIG. 5C is a partial cross-sectional schematic view of a sensor according to one embodiment of the present invention which employs a flat slip-cast sensor element.

The flat slip-cast substrate is similar to the rounded with the exception that the tip of the closed-ended tube is flat, rather than rounded. This provides the potential for greater surface area contact with the outer electrode which, in turn, provides faster response time. In the sensor shown in FIG. 5C, a flat slip-cast sensor element 100 is placed within the conductive protective sheath 20. The distal end 105 of the flat slip-cast sensor element 100 fits to contact the upper contact area 50 and possibly the side contact area 70 of the sensor tip 40 (if desired), such contact between the distal end 105 of the sensor element 100 and the sensor tip 40 permits the conductive protective sheath 20 to act as a second electrode.

The design of the sheath and sensor tip of the present invention allows all three major classes of sensor substrates to be used without necessitating different designs for each. This allows the customer or manufacturer to change the substrate to fit the intended task of the probe. For example, users of pit furnaces prefer SIRO-based probes owing to the high amount of thermal shock experienced by the probe when this type of furnace is opened. Conversely, users requiring rapid response will tend toward the flat-ended slip cast design. The sheath and sensor tip of the present invention may also be used in the modular electrolytic sensor of my patent application titled Modular Electrolytic Sensor, filed on even date of herewith and incorporated by way of reference.

What is claimed is:
1. A sensor, comprising:
   (a) a conductive protective sheath having a proximal and distal end and an outer circumference;
   (b) an internal sensor element; and

(c) a conductive end cap connected to the distal end of the conductive protective sheath and in contact with the internal sensor element;

wherein the conductive protective sheath comprises a plurality of apertures symmetrically arranged to prevent fluid flow in a straight direction of a sample fluid through the conductive protective sheath, and wherein the conductive end cap comprises cut-outs corresponding to the apertures of the conductive protective sheath.

2. The sensor of claim 1, further comprising an internal electrode located within the internal sensor element.

3. The sensor of claim 1, wherein the conductive protective sheath comprises three symmetrical arranged apertures arranged about the outer circumference of the conductive protective sheath.

4. The sensor of claim 1, wherein the apertures are configured to promote turbulent flow about the internal sensor element.

5. The sensor of claim 1, wherein the conductive end cap comprises one or more contact areas selected from the group consisting of: a side contact area, an upper contact area, and an internal indentation contact area, wherein the internal sensor element is in contact with at least one of the contact areas.

6. The sensor of claim 1, wherein the conductive end cap is in electrical contact with the internal sensor element and the conductive protective sheath.

7. The sensor of claim 1, wherein the conductive protective sheath and conductive end cap are configured to accommodate at least two of the following internal sensor elements: SIRO, round slip-cast and flat slip-cast.

8. A sensor, comprising:
(a) a conductive protective sheath having a proximal and distal end and an outer circumference;
(b) an internal sensor element;
(c) a conductive end cap connected to the distal end of the conductive protective sheath, wherein the conductive end cap comprises one or more contact areas selected from the group consisting of: a side contact area, an upper contact area, and an internal indentation contact area;

wherein the internal sensor element is in contact with at least one of the contact areas, and further wherein the conductive end cap comprises cut-outs corresponding to the apertures of the conductive protective sheath.

9. The sensor of claim 8, further comprising an internal electrode located within the internal sensor element.

10. The sensor of claim 8, wherein the conductive protective sheath comprises a plurality of apertures symmetrically arranged to prevent fluid flow in a straight direction of a sample fluid through the conductive protective sheath.

11. The sensor of claim 10, wherein the conductive protective sheath comprises three symmetrical arranged apertures arranged about the outer circumference of the conductive protective sheath.

12. The sensor of claim 10, wherein the apertures are configured to promote turbulent flow about the internal sensor element.

13. The sensor of claim 8, wherein the conductive end cap is in electrical contact with the internal sensor element and the conductive protective sheath.

14. The sensor of claim 8, wherein the conductive protective sheath and conductive end cap are configured to accommodate at least two of the following internal sensor elements: SIRO, round slip-cast and flat slip-cast.

* * * * *